(12) United States Patent
Nardi et al.

(10) Patent No.: US 8,162,863 B2
(45) Date of Patent: Apr. 24, 2012

(54) SOLE WITH ANCHOR FOR COMPRESSION FOOT CUFF

(75) Inventors: Steven Nardi, Taunton, MA (US); Malcolm G. Bock, Medfield, MA (US); David Rork Swisher, St. Charles, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 539 days.

(21) Appl. No.: 12/396,703

(22) Filed: Mar. 3, 2009

(65) Prior Publication Data

US 2009/0227922 A1 Sep. 10, 2009

Related U.S. Application Data

(63) Continuation-in-part of application No. 12/041,829, filed on Mar. 4, 2008.

(51) Int. Cl.
*A61F 5/00* (2006.01)
(52) U.S. Cl. .......................... 602/13; 602/23
(58) Field of Classification Search .......... 601/148–152, 601/DIG. 20; 602/13; 36/93, 88, 89, 29; 606/201, 202, 203; 128/DIG. 20
See application file for complete search history.

(56) References Cited

U.S. PATENT DOCUMENTS

| | | | |
|---|---|---|---|
| 2,183,277 A | 12/1939 | Heilhecker | |
| 3,786,805 A | 1/1974 | Tourin | |
| 4,013,069 A | 3/1977 | Hasty | |
| 4,029,087 A | 6/1977 | Dye | |
| 4,030,488 A | 6/1977 | Hasty | |
| 4,187,620 A | 2/1980 | Selner | |
| 4,696,289 A * | 9/1987 | Gardner et al. | 601/152 |
| 4,805,601 A | 2/1989 | Eischen, Sr. | |
| RE32,939 E * | 6/1989 | Gardner et al. | 601/152 |
| RE32,940 E * | 6/1989 | Gardner et al. | 601/152 |
| 4,887,369 A | 12/1989 | Bailey | |
| 5,199,191 A | 4/1993 | Moumdjian | |
| 5,321,901 A | 6/1994 | Kelly | |
| 5,345,260 A | 9/1994 | Petralia | |
| 5,354,260 A * | 10/1994 | Cook | 602/13 |
| 5,407,421 A * | 4/1995 | Goldsmith | 602/5 |
| 5,462,517 A | 10/1995 | Mann | |
| 5,464,385 A | 11/1995 | Grim | |
| 5,626,556 A | 5/1997 | Tobler | |
| 5,718,669 A | 2/1998 | Marble | |

(Continued)

FOREIGN PATENT DOCUMENTS

EP 1795167 A1 6/2007

(Continued)

OTHER PUBLICATIONS

Office action issued Sep. 2, 2011 in related U.S. Appl. No. 12/041,829—14 pgs.

(Continued)

*Primary Examiner* — Patricia Bianco
*Assistant Examiner* — Raymond E Harris
(74) *Attorney, Agent, or Firm* — Thomas M. Johnston, Esq.

(57) ABSTRACT

A compression foot cuff includes a counterforce component adjacent to a first impermeable layer of an inflatable member. The counterforce component includes a generally rigid sole for applying a counterforce to the inflatable member and an anchor member extending outward from the sole. The anchor member is secured to or formed as one piece with the port to position the sole with respect to the inflatable member.

10 Claims, 8 Drawing Sheets

U.S. PATENT DOCUMENTS

| | | | |
|---|---|---|---|
| 5,795,312 | A | 8/1998 | Dye |
| 5,848,482 | A | 12/1998 | Bathum |
| 5,931,797 | A * | 8/1999 | Tumey et al. ............ 601/152 |
| 5,954,676 | A | 9/1999 | Kramer, III |
| 5,989,204 | A | 11/1999 | Lina |
| 6,014,823 | A | 1/2000 | Lakic |
| 6,098,313 | A | 8/2000 | Skaja |
| 6,231,532 | B1 | 5/2001 | Watson et al. |
| 6,319,215 | B1 * | 11/2001 | Manor et al. ............ 601/152 |
| 6,358,219 | B1 | 3/2002 | Arkans |
| 6,585,669 | B2 * | 7/2003 | Manor et al. ............ 601/152 |
| 6,592,534 | B1 * | 7/2003 | Rutt et al. ............ 601/151 |
| 6,685,661 | B2 * | 2/2004 | Peled ............ 601/149 |
| 6,736,787 | B1 | 5/2004 | McEwen et al. |
| 7,246,453 | B2 | 7/2007 | Kim |
| 2001/0018564 | A1 * | 8/2001 | Manor et al. ............ 601/152 |
| 2004/0064976 | A1 * | 4/2004 | Barteet ............ 36/100 |
| 2005/0143682 | A1 * | 6/2005 | Cook et al. ............ 601/151 |
| 2007/0282233 | A1 | 12/2007 | Meyer et al. |
| 2009/0227917 | A1 | 9/2009 | Nardi |
| 2009/0227918 | A1 | 9/2009 | Nardi et al. |
| 2009/0227919 | A1 | 9/2009 | Nardi et al. |
| 2009/0227920 | A1 | 9/2009 | Nardi et al. |
| 2009/0227921 | A1 | 9/2009 | Nardi |

FOREIGN PATENT DOCUMENTS

JP     11-197201 A     7/1999

OTHER PUBLICATIONS

Response filed Nov. 16, 2011 to Office Action dated Sep. 2, 2011 regarding U.S. Appl. No. 12/041,829—20 pgs.

* cited by examiner

SOLE WITH ANCHOR FOR COMPRESSION FOOT CUFF

FIELD OF THE INVENTION

The present invention generally relates to a sole for a compression foot cuff, and more particularly to such a sole with an anchor.

BACKGROUND

Compression devices for applying compressive forces to a selected area of a wearer's anatomy are generally employed to improve blood flow in the selected area. Compression devices that provide intermittent pulses of a compressed fluid (i.e. air) to inflate at least one inflatable chamber in a cuff or sleeve are particularly useful. This cyclic application of pressure provides a non-invasive method of prophylaxis to reduce the incidence of deep vein thrombosis (DVT), and the like. These compression devices find particular use during surgery on patients with high-risk conditions such as obesity, advanced age, malignancy, or prior thromboembolism. Patients who develop this condition often have swelling (edema) and tissue breakdown (venous stasis ulcer) in the lower leg. When a DVT occurs, the valves that are located within the veins of the leg can be damaged, which in turn can cause stasis and high pressure in the veins of the lower leg.

Generally, these compression devices are fluidly coupled to a source of pressurized fluid by one or more air tubes. Additionally, each compression device includes a flexible shell having one or more bladders disposed therein. The compression device is placed around the patient's foot or other selected portion whereupon a pressurized fluid is delivered into the bladder creating pressure at the part or parts of the body in contact with the bladder.

Compression cuffs adapted for use with a patient's foot may be used by themselves or combined with one or more additional compression cuffs or sleeves that are disposed on portions of a patient's leg for improving the treatment regimen. In general, each of the additional compression sleeves includes a plurality of separate inflatable chambers that are progressively arranged along a longitudinal axis of the sleeve from a lower portion to an upper portion of the limb. A pressure source, e.g. a controller, is provided for intermittently forming a pressure pulse within these inflatable chambers from a source of pressurized fluid during periodic compression cycles. The compression sleeves provide a pressure gradient along the patient's limbs during these compression cycles which progressively decreases from the lower portion to the upper portion of the limb (e.g. from the ankle to the thigh).

Compression cuffs that are adapted for use with a patient's foot generally include a heel strap with a tab portion that is adapted to fit around a portion of the patient's heel. This arrangement allows the compression cuff to be wrapped around and releasably attached to the patient's foot. The compression cuff may include a generally rigid sole to direct expansion of the inflatable chamber toward the wearer's foot. The rigid sole needs to be located under that portion of the inflatable member that is acting on the portion of the foot to produce blood flow out of the foot. Conventionally, the rigid sole is temporarily attached to the bladder by double stick tape. Final location and positioning of the rigid sole may be carried out by stitching. For example, the bladder is typically stitched to an outer wrap of the foot cuff. The stitching can be arranged so that it captures the rigid sole in position relative to the bladder, as well as the outer wrap. This requires care and precision in manufacturing the foot cuff.

Examples of compression cuffs are disclosed in U.S. Pat. Nos. 4,013,069 and 4,030,488 to Hasty, U.S. Pat. Nos. 4,029,087 and 5,795,312 to Dye, U.S. Pat. No. 5,626,556 to Tobler et al., and U.S. patent application Ser. No. 11/761,212 to Meyer et al., all of which are currently owned by Tyco Healthcare Group LP and are incorporated by reference herein in their entireties. Other examples of compression cuffs are disclosed in U.S. Pat. No. 4,696,289 to Gardner et al., U.S. Pat. No. 5,989,204 to Lina and U.S. Pat. No. 5,345,260 to Cook. An example of compression treatment method is disclosed in U.S. Pat. No. 6,231,532 to Watson et al., which is owned by Tyco Healthcare Group LP, the contents of which are hereby incorporated by reference herein in their entirety.

SUMMARY

In one aspect, a compression foot cuff for applying compression to a wearer's foot generally comprises an inflatable member including first and second fluid impermeable layers secured to one another to define an inflatable chamber. A port extends outward from the first fluid impermeable layer in fluid communication with the inflatable chamber. A counterforce component adjacent to the first impermeable layer of the inflatable member includes a generally rigid sole generally opposing the first impermeable layer for applying a counterforce to the inflatable member and an anchor member extending outward from the sole. The anchor member is secured to the port to position the sole with respect to the inflatable member.

In another aspect, a method of making a compression foot cuff for applying compression to a foot of a wearer generally comprises forming a bladder by joining together generally opposed first and second layers of fluid impermeable material. A port is attached to the first impermeable layer of fluid impermeable material. An anchor of a counterforce component is attached to the port to position a generally rigid sole of the counterforce component relative to the bladder.

In yet another aspect, a counterforce component for a compression foot cuff of the type including a bladder for applying compression to a foot of a wearer generally comprises a generally rigid sole sized and shaped to lie in generally opposing relationship with a bottom of a wearer's foot. An anchor member extends outward from the sole for securing the anchor member to the foot cuff and for positioning the sole relative to bladder when the anchor member is secured to the foot cuff.

Other features will be in part apparent and in part pointed out hereinafter.

DETAILED DESCRIPTION OF THE DRAWINGS

Referring now to the drawings, a compression foot cuff for applying compressive pressure to a wearer's foot is generally indicated at 10. The foot cuff is adapted for use in a compression therapy system, which further includes a supply of pressurized air (not shown) and tubing connecting the supply of pressurized air to the foot cuff.

Figure 1:
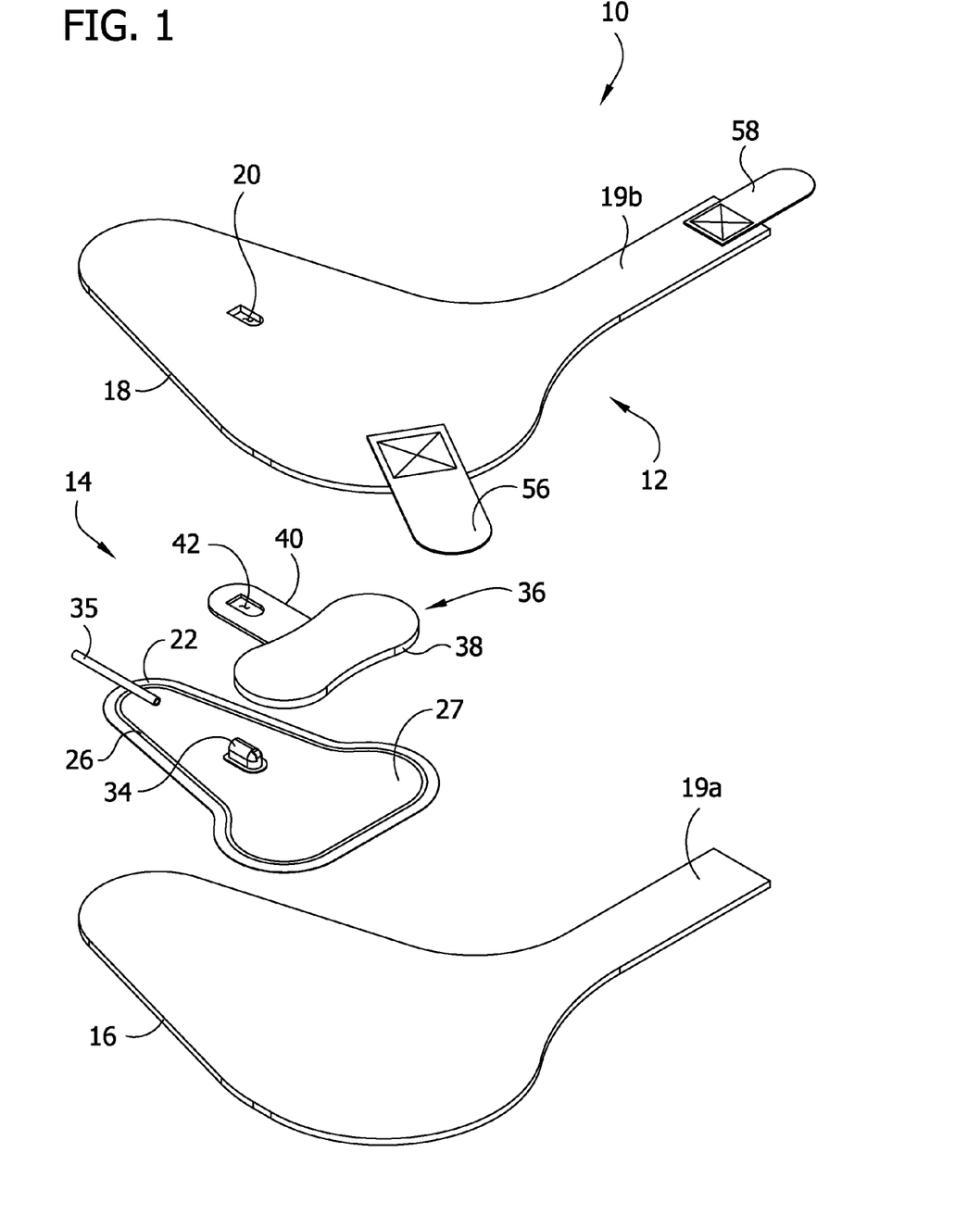
FIG. 1 is an exploded perspective of a first embodiment of a compression foot cuff in accordance with the present disclosure.

As shown best in FIG. 1, the foot cuff 10 includes an envelope, generally indicated at 12, substantially enveloping or enclosing a bladder, generally indicated at 14. The envelope 12 includes an inner contact layer 16 and an outer layer 18 secured to one another generally adjacent to corresponding perimeters of the layers to define an interior space for receiving and substantially enclosing the bladder 14 (broadly, "an inflatable member") therein. The contact layer 16 and the outer layer 18 may be fixedly secured to one another at their peripheral edge margins, such as by heat welding, adhesives, sewing or other suitable ways. Alternatively, the contact layer 16 and the outer layer 18 may be releasably secured to one another. In use the contact layer 16 is adjacent to the wearer's foot and the outer layer 18 is located farthest from the foot. As used herein, the terms "inner" and "outer" indicate relative positions of respective components and surfaces with respect to the skin of the wearer's body part when the compression device is secured to the body part, and as such, an "inner" component or surface is more adjacent to the skin of the body part than an "outer" component or surface.

Contact layer 16 and outer layer 18 of the envelope 12 include ankle strap portions 19a and 19b respectively. Ankle strap portions 19a, 19b have a longitudinally projecting configuration for wrapping about a portion of the foot adjacent to the ankle. The ankle strap portions 19a, 19b can be sewn, RF welded, or sonic welded. However, in the illustrated embodiments, the ankle strap portions 19a, 19b are formed as one piece with the contact layer 16 and outer layer 18, respectively.

Contact layer 16 of the envelope 12 is adapted for contacting the foot. Contact layer 16 is in one embodiment fabricated from a chemically treated material, with wicking ability, for wicking away moisture from the skin. In one embodiment, contact layer 16 includes a mesh-like fabric capable of wicking moisture away from the patient's skin. Furthermore, the contact layer 16 can be faced with a soft material toward the treatment surface of the patient. For example, the material can be a thin layer of open celled porous foam, napped cloth, or a layer of vapor permeable cloth. It is understood that the cuff 12 may not include a contact layer within the scope of the present invention.

Outer layer 18 of the envelope 12 includes an opening 20 for permitting a pressurized fluid inlet passage therethrough. Outer layer 18 is configured for providing the attachment surface for a hook and loop feature of cuff 12, as will be described in more detail herein below. Moreover, the outer layer 18 provides a soft material for cushioning effect against the top portion of the feet and may be fabricated from similar materials as contact layer 16 and in similar dimensions therewith for corresponding geometry. Alternatively, outer layer 18 may be fabricated from a laminated material, such as, for example, sontara fabric, open cell urethane foam, or loop fabric. It is understood that the cuff 12 may not include an outer layer within the scope of the present invention.

Figure 4:
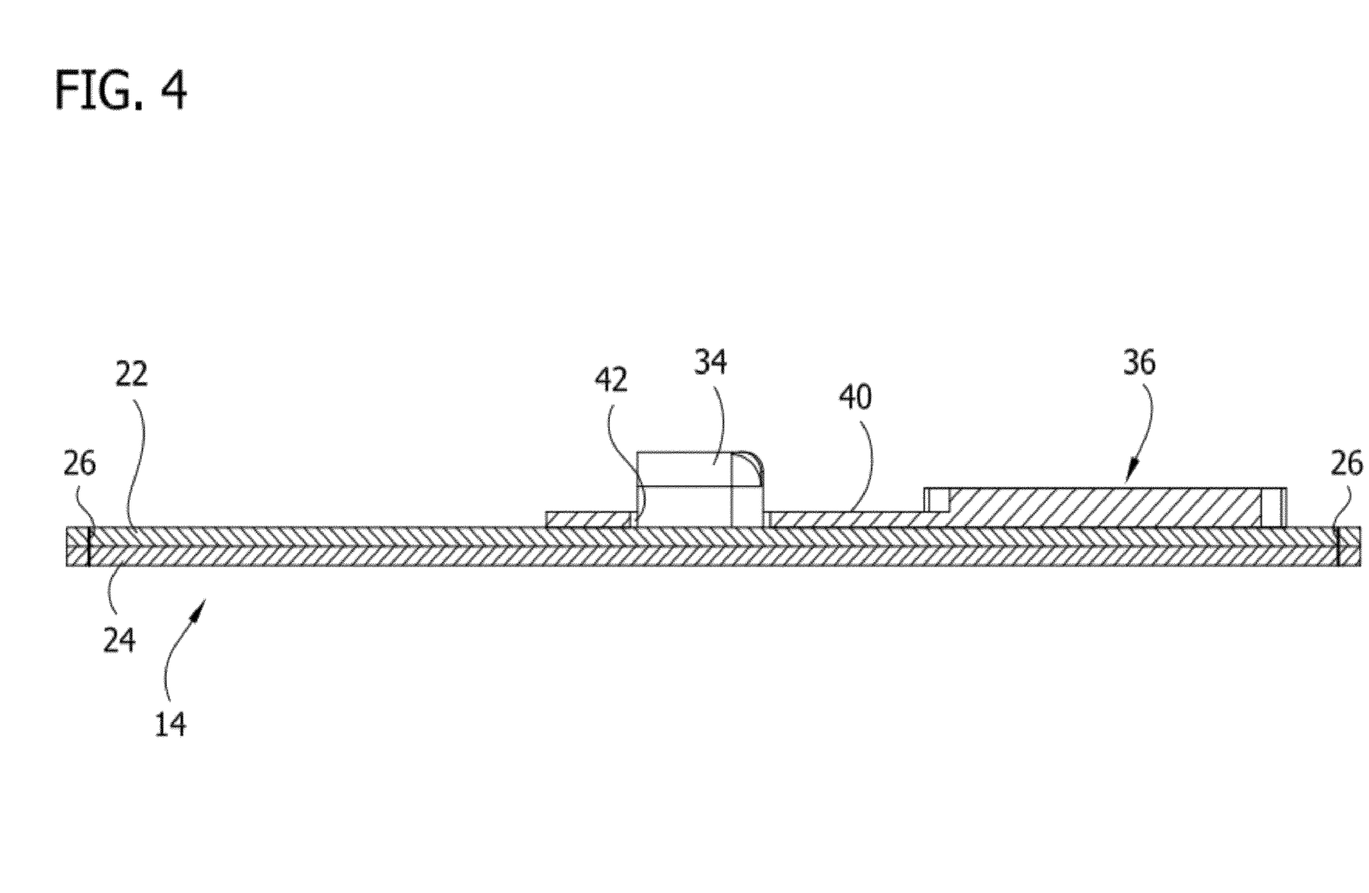
FIG. 4 is a section of the bladder with the attached sole taken along the line 4-4 in FIG. 2.
Figure 4A:
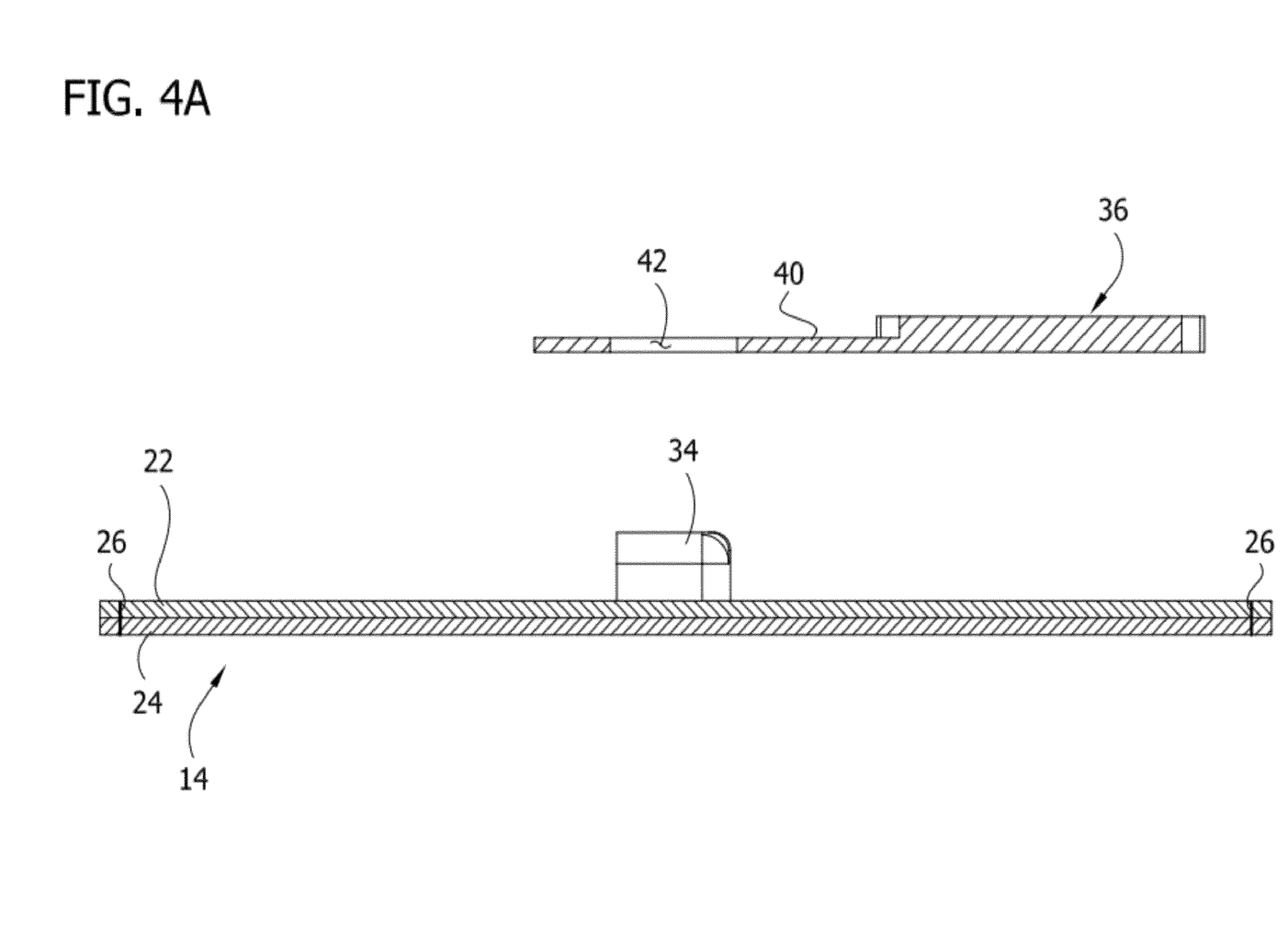
FIG. 4A is an exploded FIG. 4.

The bladder 14 is configured for positioning against the bottom portion of the foot. Referring to FIG. 4, bladder 14 includes outer and inner layers 22, 24 of air impermeable material (e.g., PVC) joined together in a suitable manner along a line 26 adjacent to their peripheries to define a single inflatable chamber 27. The layers 22, 24 may be joined to one another in a suitable manner such as by radio frequency (RF) welding. Other ways of joining the layers 22, 24 include sewing, adhesive, heat sealing, etc. It is understood that the bladder 14 can include more than one inflatable chamber 27 within the scope of the present invention. The inflatable chamber 27 of the bladder 14 is adapted for receiving and retaining a pressurized fluid (e.g. air) for exerting compressive pressure to the foot during successive pressure application cycles. The inflatable chamber 27 has a port 34 and a tube 35 connected to the port for air or fluid to be introduced into the chamber during the start of a compression cycle and to be exhausted to end the compression cycle. The port 34 of the illustrated embodiment is a plastic component that is secured such as by heat welding or other means to the bladder 14. It is understood that other ways of introducing air or fluid into the chamber 27 are within the scope of the invention.

A counterforce component, generally indicated at 36, is disposed between the outer layer 18 of the envelope 12 and the outer layer 22 of the bladder 14. The counterforce component 36 generally includes a generally rigid sole 38, an anchor member 40, and the port 34. It is believed the sole 38 provides a counterforce to the outer layer 22 of the bladder 14 as the bladder is expanding to direct expansion toward the contact layer 16 and the user's foot. In this way, the inner layer 24 expands outward more than the outer layer 22 to direct compressive force toward the user's foot. The sole 38 may be constructed from a polypropylene material or other material within the scope of the invention.

Figure 2:
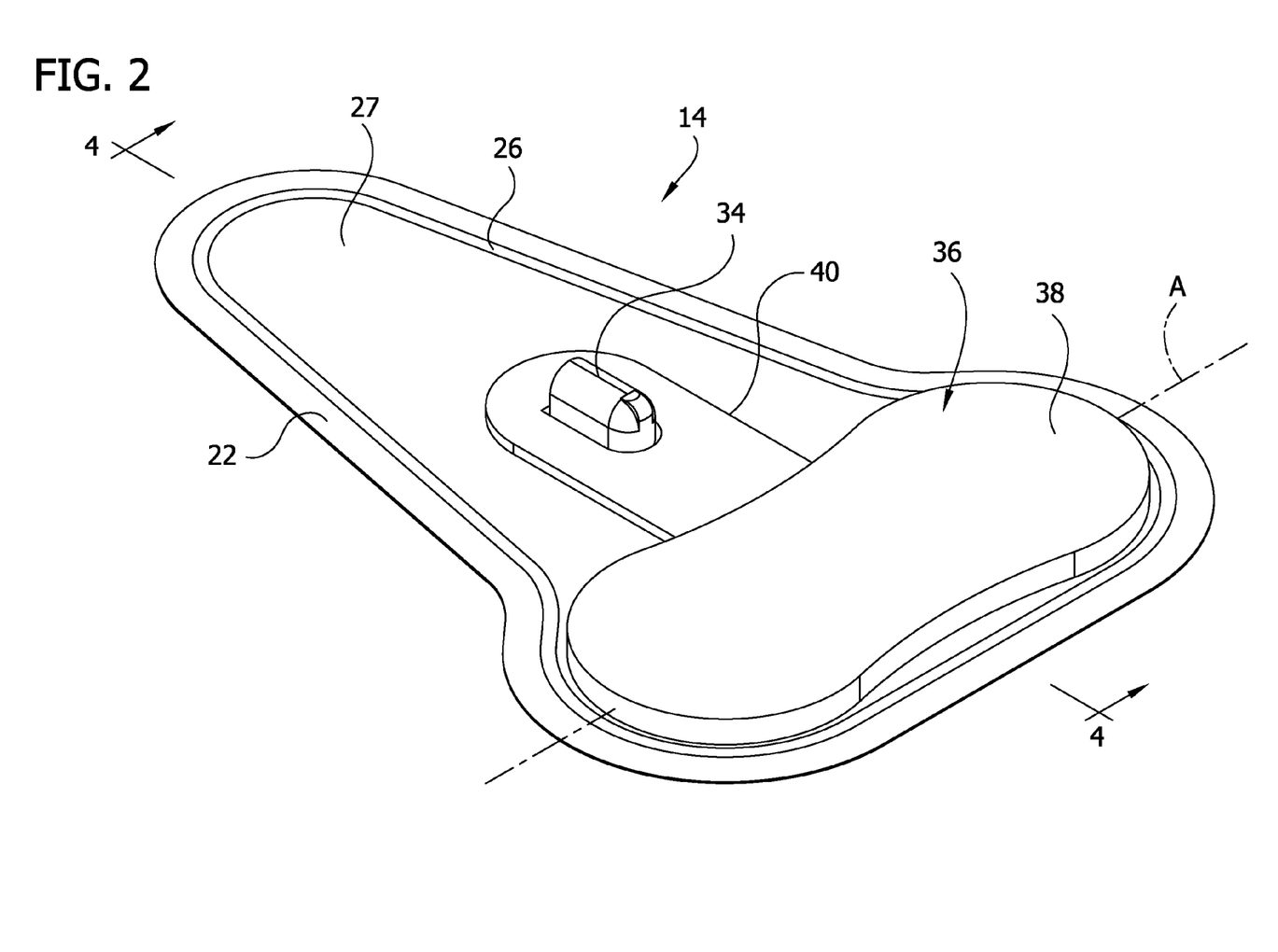
FIG. 2 is a perspective of a bladder of the foot cuff with a sole attached thereto.
Figure 3:
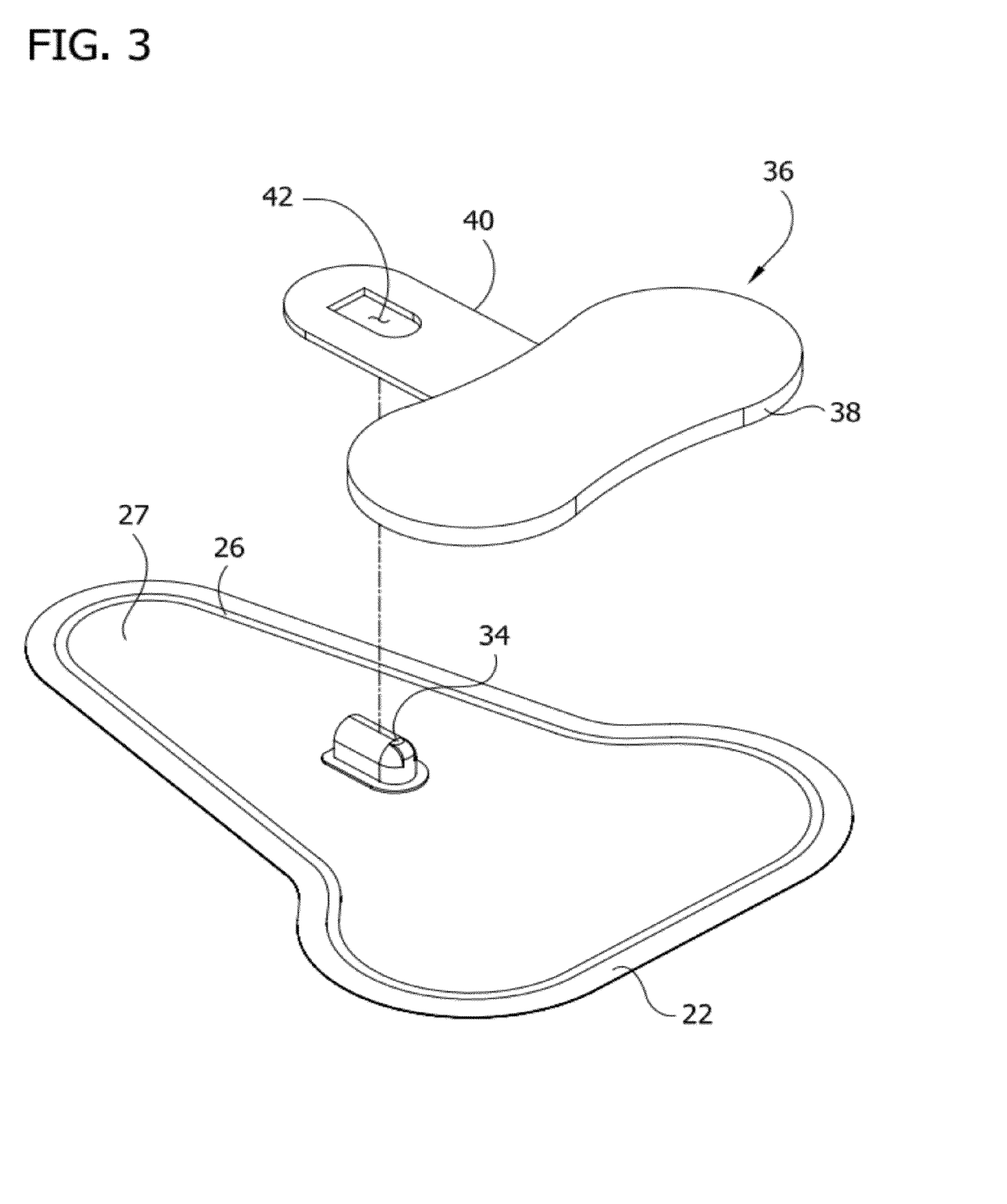
FIG. 3 is an exploded view of FIG. 2.

In the illustrated embodiment, the anchor member 40 comprises a strap that is relatively flexible when compared to the generally rigid sole. In one example, and for reasons explained below, the strap 40 resists bending in-plane more than it resists bending out-of-plane. The strap 40 extends laterally outward from the sole 38 with respect to a major axis A of the sole (FIG. 2). An opening 42 in the strap 40 generally overlies the opening 20 in the outer layer 18 of the envelope 12. The port 34 extends from the outer impermeable layer 22 of the bladder 14, through the opening 42 in the strap 40 and through the opening 20 in the outer layer 18 of the envelope 12. The strap 40 is secured to the outer layer 18 of the bladder 14 through this arrangement. Adhesive or other auxiliary ways of securing the strap 40 to the port 34 are contemplated. Moreover, the port (not shown) could be formed to mechanically capture the strap 40 when secured to the outer layer 22 of the bladder 14. Further, the strap 40 may be secured to the outer layer 18 of the bladder 14 in other ways. The strap 40 is sized, shaped and positioned on the counterforce component 36 so that when the strap is secured to the bladder 14 by inserting the port 34 through the opening 42 in the strap, the sole is positioned in generally opposing relationship with that portion of the bladder 14 that will act on a bottom of a wearer's foot. In the illustrated embodiment, the thickness of the strap 40 would be from about 20 thousandths of an inch (0.020 in) to about 40 thousandths of an inch (0.040 in). The sole 38 is between about 150 thousandths of an inch (0.150 in) and about 190 thousandths of an inch (0.190 in), and preferably about 160 thousandths of an inch (0.160 in). The strap, if formed separately from the sole, could be secured in any number of ways to the sole. For example, the sole could be made in two pieces and the strap sandwiched between the pieces. The strap could also be attached, for example, by heat welding or by adhering to the side of the sole.

As stated above, in one example the strap 40 resists bending in-plane more than it resists bending out-of-plane. Through this configuration, the strap 40 retains the sole 38 in position relative to the bladder 14 while allowing the strap to flex or bend as the foot cuff 10 is wrapped around the wearer's foot. It is understood that in other embodiments, the strap 40 may resist both in-plane and out-of-plane bending to the same extent without departing from the scope of the present invention. Moreover, the strap 40 preferably provides some resistance to bending out of plane to prevent folding of the strap during assembly of the cuff.

Hook fasteners 56, 58 are provided for securing the wrapped cuff 12 around a foot, and are positioned on the outer layer 18 of the cuff. Hook fastener 56 is mounted to strap portion 19b of outer layer 18 of foot cuff 12 while hook fastener 58 is mounted on a surface of outer layer 18. In use, when ankle strap portions 19a, 19b are wrapped about the back of the foot, hook element 56 engages outer layer 18 to facilitate mounting of foot cuff 12 on the foot. An identification tab (not shown) may also be included for providing information such as the model number and manufacturer name. Hook fasteners 56, 58 may have tabs (not shown) without fastening material thereon to provide convenient gripping locations on the hook fasteners to thereby allow the practitioner to easily remove the hooks from the outer face 18b of outer layer 18. The use and operation of the foot cuff 12 for applying compression therapy to the wearer's foot is generally known in the art and will not be described herein.

Figure 5:
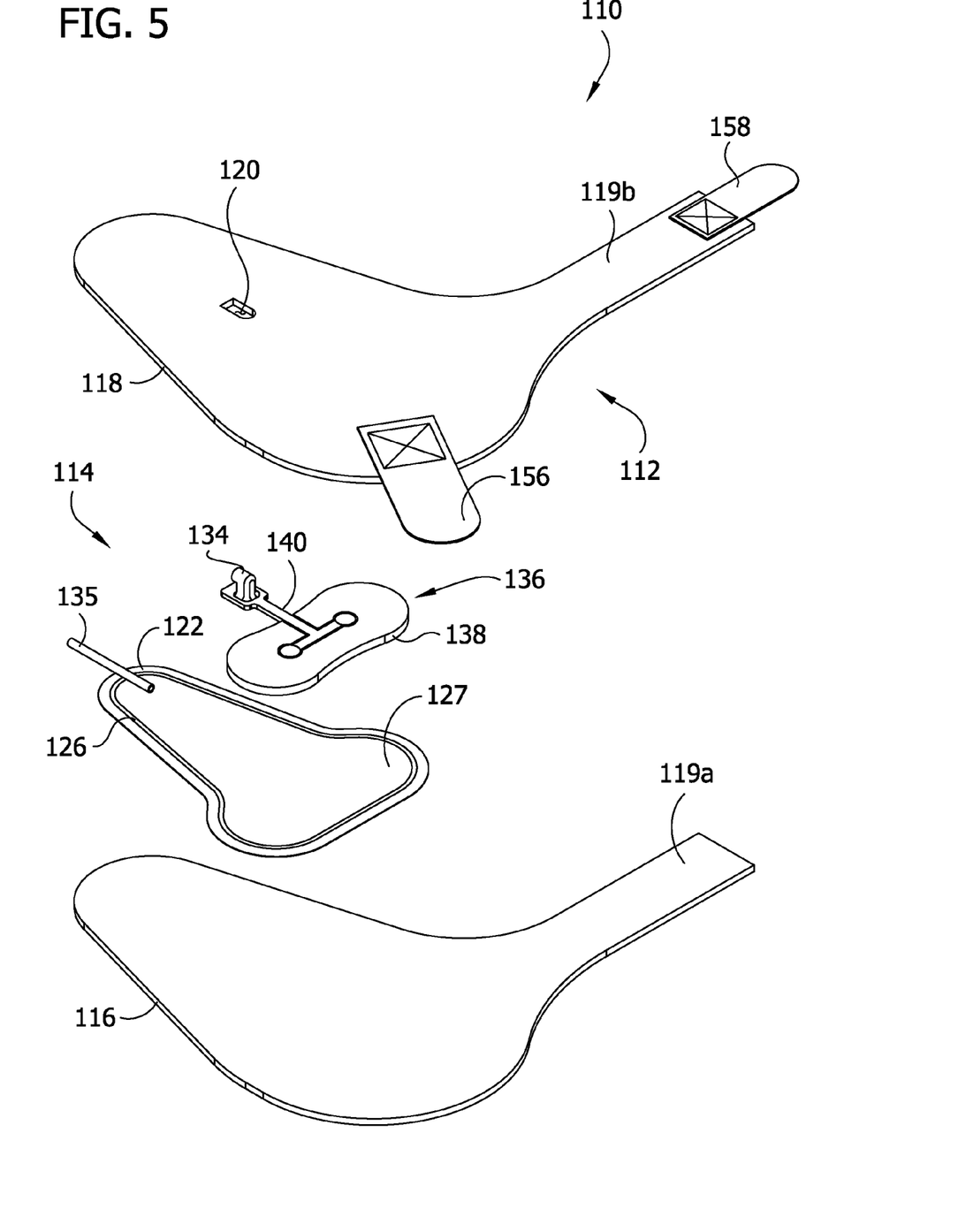
FIG. 5 is a perspective of second embodiment of a compression foot cuff in accordance with the present disclosure.
Figure 6:
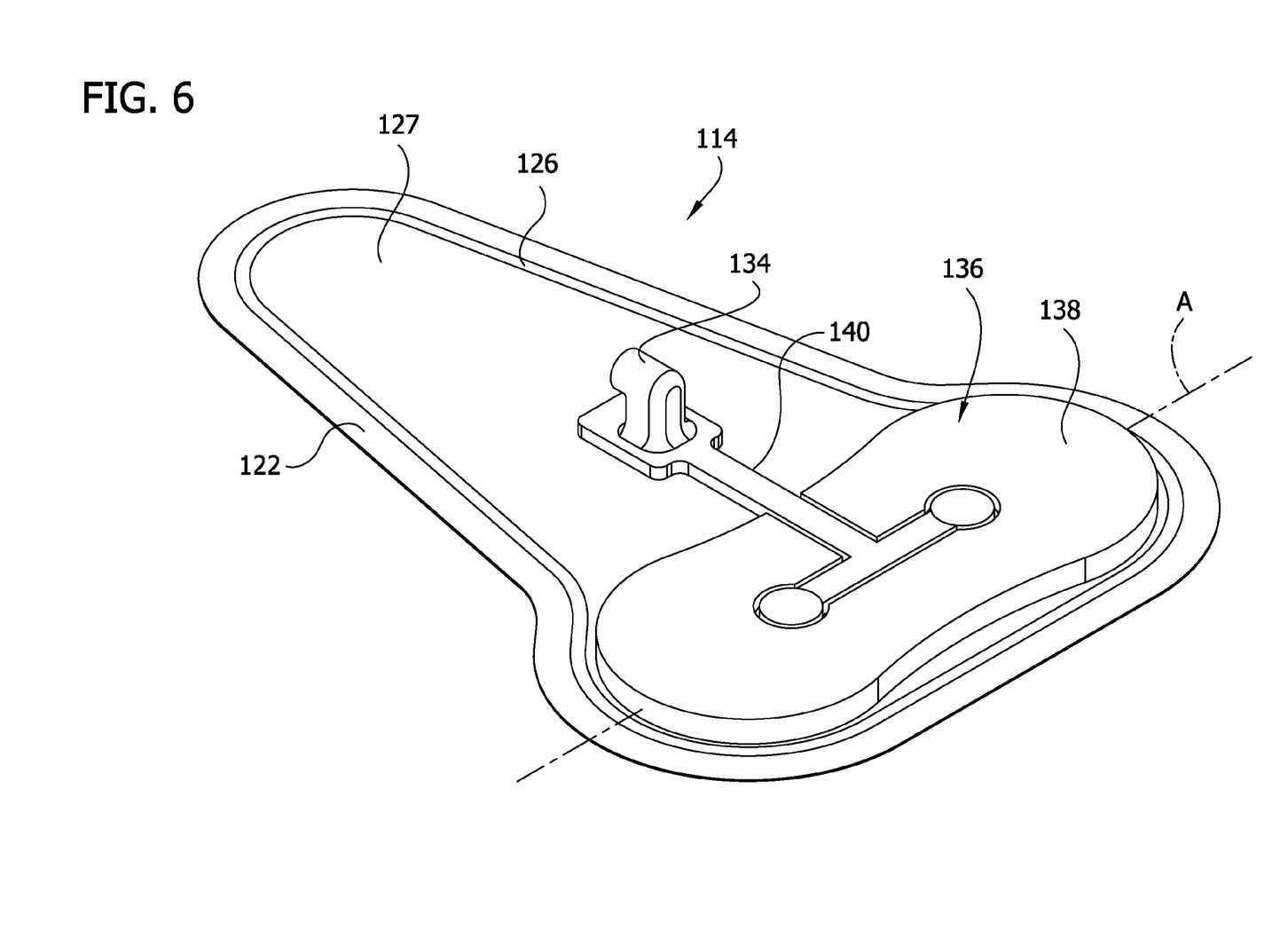
FIG. 6 is a perspective of a bladder of the foot cuff with a sole attached thereto.
Figure 7:
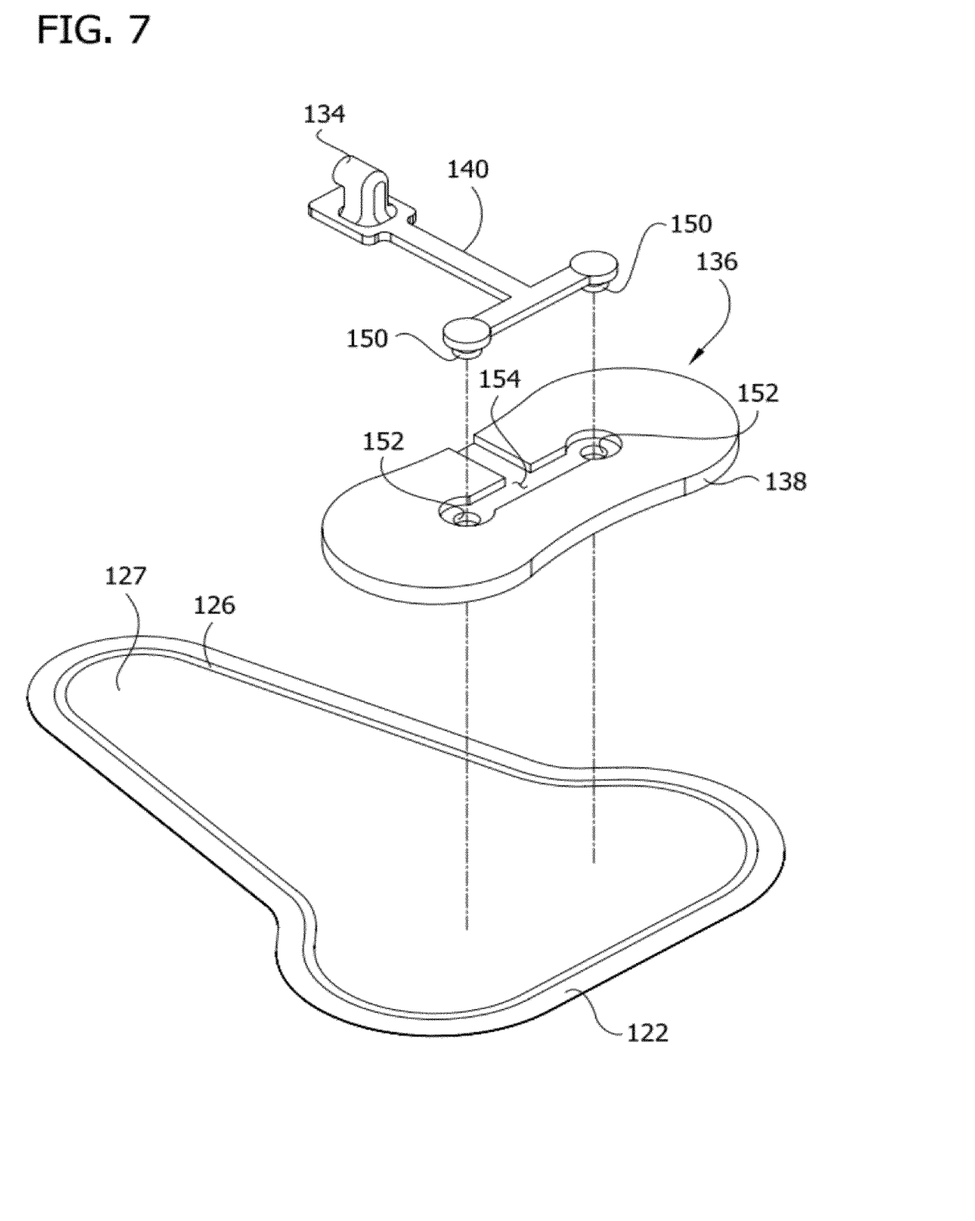
FIG. 7 is an exploded view of FIG. 6.

Referring to FIGS. 5-7, a second embodiment of a compression foot cuff is generally indicated at 110 (FIG. 5). This second embodiment is similar to the first foot cuff 10, and like components are indicated by corresponding reference numerals plus 1 00. A difference between the second foot cuff 110 and the first foot cuff 10 is that a counterforce component 136 of the second foot cuff includes an anchor member 140 comprising a strap that is formed integrally with a port 134. The strap 140 and the port 134 may be integrally formed as a one-piece structure such as by molding or in other ways without departing from the scope of the invention. The strap 140 may have similar mechanical properties as the strap 40 of the first embodiment, disclosed above. The strap 140 is attached to a generally rigid sole 138 of the counterforce component 136 by snap-fit connection. In the illustrated embodiment (FIG. 7), a pair of male snap components 150 on the strap 140 snap into complementary female snap components 152 of the sole 138. Other ways of securing the strap 140 to the sole 138 may be used within the scope of the present invention. A recess 154 in a face of the sole 138 receives heads of the male snap components and an overlapping portion of the strap 140 so that the heads of the male snap components and the overlapping portion do not extend substantially past the face of the sole. This arrangement provides an integral and generally planar look, and provides more comfort to the wearer.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A compression foot cuff for applying compression to a wearer's foot comprising:
    an inflatable member including first and second fluid impermeable layers secured to one another to define an inflatable chamber;
    a port extending outward from the first fluid impermeable layer in fluid communication with the inflatable chamber;
    a generally rigid sole generally opposing the first impermeable layer for applying a counterforce to the inflatable member;
    and an anchor member interconnecting the port and the sole to position the sole with respect to the inflatable member, the anchor member comprising a strap extending outward from the sole, the strap being relatively flexible compared to the sole,
    wherein the strap and the port are integrally formed as one piece of material separate from the sole, wherein the strap is attached to the sole by a mechanical connection.

2. A compression foot cuff as set forth in claim 1 further comprising an outer layer generally adjacent to the sole so that the sole is disposed between the outer layer and the first impermeable layer of the inflatable member, the outer layer including an opening, the port extending through the opening in the outer layer so that the port is generally accessible, wherein the outer layer includes an ankle strap portion configured for wrapping around a portion of the wearer's foot adjacent to the wearer's ankle.

3. A compression foot cuff as set forth in claim 2 wherein the strap and the sole include mateable snap-fit connectors, wherein the strap is attached to the sole by snap-fit connection of the mateable snap-fit connectors.

4. A compression foot cuff as set forth in claim 1 wherein the sole defines a recess in a face of the sole, an overlapping portion of the strap being received in the recess.

5. A compression foot cuff as set forth in claim 4 wherein the recess is sized and shaped such that the overlapping portion of the strap does not extend beyond a plane defined by the face of the sole.

6. A compression foot cuff as set forth in claim 1 wherein the strap extends laterally outward from the sole.

7. A compression foot cuff as set forth in claim 1 wherein the strap and the sole include mateable snap-fit connectors, wherein the strap is attached to the sole by snap-fit connection of the mateable snap-fit connectors.

8. A method of making a compression foot cuff for applying compression to a foot of a wearer, the method comprising:
    forming a an inflatable member by joining together generally opposed first and second layers of fluid impermeable material;
    attaching a port to the first impermeable layer of fluid impermeable material, wherein a strap is integrally formed with the port as one piece of material separate from a generally rigid sole and extends outward therefrom;
    attaching the strap to the generally rigid sole by a mechanical connection to position the sole relative to the inflatable member.

9. A method of making a compression foot cuff as set forth in claim 8 further comprising enveloping the inflatable member and the sole in an envelope comprising a contact layer and an outer layer secured together along one another's peripheries.

10. A method of making a compression foot cuff as set forth in claim 8 wherein said attaching the strap to a generally rigid sole by a mechanical connection comprises mating a first snap-fit connector of the strap with a second snap-fit connector of the sole to form a snap-fit connection.

* * * * *